United States Patent [19]

Hernandez et al.

[11] Patent Number: 4,944,302
[45] Date of Patent: Jul. 31, 1990

[54] ELECTRONIC DEVICE FOR COSMETIC AND MEDICAL THERAPY

[75] Inventors: Epifanio J. Hernandez; José C. Benach, both of Barcelona, Spain

[73] Assignee: Indiba, S.A., Barcelona, Spain

[21] Appl. No.: 267,510

[22] Filed: Oct. 26, 1988

Related U.S. Application Data

[63] Continuation of Ser. No. 880,717, Jul. 11, 1986, abandoned.

[30] Foreign Application Priority Data

Jul. 8, 1985 [ES] Spain .................................. 287964
Dec. 12, 1985 [ES] Spain .................................. 549883

[51] Int. Cl.$^5$ .............................................. A61N 1/40
[52] U.S. Cl. .................................. 128/422; 128/804; 128/800; 128/24.1
[58] Field of Search .......................... 128/790–796, 128/800, 801, 803, 804, 24.1, 24.4, 24.5, 422

[56] References Cited

U.S. PATENT DOCUMENTS

4,427,001 1/1984 Kiefer et al. .................... 128/24.4
4,669,480 6/1987 Hoffman ........................ 128/804

Primary Examiner—Lee S. Cohen
Assistant Examiner—David Shay
Attorney, Agent, or Firm—McGlew & Tuttle

[57] ABSTRACT

An electronic device and method for use in cosmetic and medical treatment of a person by application of electrodes to a person's skin. The device includes a high frequency oscillating circuit for supplying high frequency current in the range of from 1 to 2 megacycles per second. The high frequency oscillating circuit automatically reduces the supply power when the load impedance of the person is lowered. The high-frequency oscillating circuit includes an oscillating circuit producing an oscillation signal, a preamplifier boosting the oscillating circuit and an amplifier receiving the boosted oscillating circuit and outputting an amplified oscillating signal. Resonance circuit means are provided receiving the amplified oscilliating signal and outputting an oscillating signal with resonance at an operating frequency. An output amplifier is preferably connected to the resonance circuit receiving a signal output by the resonant circuit and outputting an amplified at an operating frequency. A high-frequency transformer is provided having a first and second winding and a center housing adjacent the second transformer winding having an aluminum cylinder for dissipating heat and reducing the load inductance of the first and second winding so as to increase the resonance frequency. The device includes an electrical current application element which is connected to the second winding of the transformer apparatus for transmitting high frequency current capacitively to the epidermis of the person being treated. Both an active electrode and a neutral return electrode are provided to avoid dispersion of electric current flow.

2 Claims, 2 Drawing Sheets

ELECTRONIC DEVICE FOR COSMETIC AND MEDICAL THERAPY

This is a continuation application of application Ser. No. 880,717 filed July 1, 1986, now abandoned.

FIELD AND BACKGROUND OF THE INVENTION

The present invention relates to the field of electronic devices, particularly used for cosmetic and medical treatment.

SUMMARY AND OBJECTS OF THE INVENTION

The present invention refers to a method and device for cosmetic and medical therapy, essentially comprising an electronic circuit for generating generally high frequency signals and a tool made up with an active electrode of very peculiar features which includes a specific shape suitable to accomplish the purpose of the device. The device is useful in medical treatment, particularly for pain treatment and dermatology or within the cosmetic field for complexion regeneration and depilation.

This device performs these functions by locally applying oscillating energy on the pertinent body zones, in a capacitive manner. According to the invention, the active electrode, being metallic, does not directly come into contact with the epidermis. Instead, a sheet of insulating material is interposed between the epidermis and the active electrode so use of the device does not involve any danger whatsoever for the patient; surprising effects are obtained therefrom and in most cases immediately and in other cases a short time thereafter.

Operation frequency of this device is in the order of 1 to 2 megacycles per second and the required power for its generation is moderate, which in turn brings out a lower energy consumption defining thereby a greater performance (or efficiency). The device includes at least a neutral or return electrode and a special tool for the development of the treatment. This tool is being powered by the high frequency current.

The resulting dispersion or non-utilized oscillating energy in the use of this electronic device is minimum and basically due to two factors: the first being brought out by the use of a return arrangement which remarkably increases the exploitation of energy and therefore the performance, and the second relates to the ability of the distance/frequency ratio, for which the average value of the load impedance shown by the human body has been accounted for.

The power supplied by this device is related to the impedance value of the device and due to the local application of oscillating energy, thereby making practically impossible the production of skin burns.

The active electrode is electrically insulated. With this electrode, contact is made and/or massage against the epidermis area to be treated by prior application of a moisturizing cream. The general electronic circuit includes several stages. The output stage transformer has a housing wherein an aluminum cylinder is arranged with the double function of dissipating any heat generated by the transformer and to reduce any inductance with the subsequent increase in the resonance frequency.

Accordingly, it is an object of the invention to provide an electronic device for cosmetic and medical use in which an oscillating circuit is provided to produce a general highfrequency signal. The circuit includes means for automatically reducing the applied power when the load impedance is lowered, thereby reducing the potential of burning a person treated. The output of the oscillating circuit is electrically fed to an active tool which transmits the high frequency current to the patient's body area. The active tool includes at least a neutral electrode (or return electrode) which is applied to the epidermis of the patient which thereby avoids dispersion of the electrical current flow.

The oscillating circuit includes a transistor which amplifies a signal and applies the signal to an excitation transistor. The signal from the excitation transistor is directed to a resonant circuit which emits a signal which is amplified by an output transistor. A high frequency transformer is provided which includes a center housing with an aluminum cylinder which is inserted for dissipating any heat generated by the transformer and to reduce the load inductance so as to increase the resonant frequency.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive matter in which a preferred embodiment of the invention is illustrated.

DESCRIPTION OF THE PREFERRED EMBODIMENT

Figure 1:
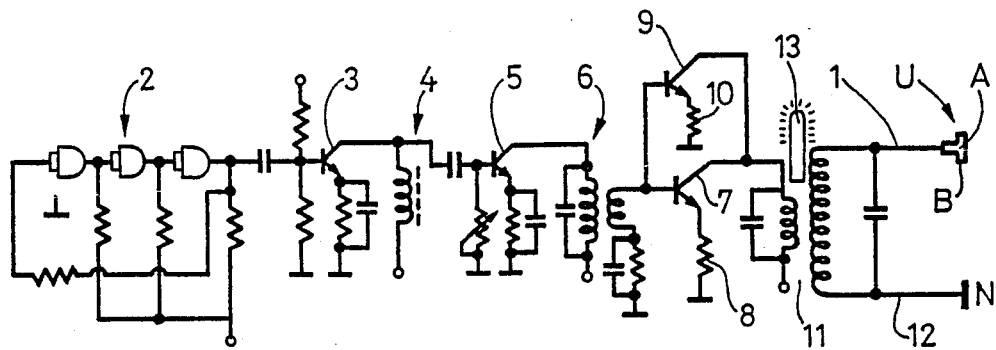
FIG. 1 shows a diagram of the electronic circuit of this device.

Reference U generally designates a special active tool which is to be applied to the epidermis and is variable in accordance with the treatment needed. This tool U receives the high frequency oscillations or high frequency oscillation signals emitted from a lead 1. An electronic circuit is provided including an oscillating stage 2 provided in the form of an integrated circuit (IC). The oscillating stage 2 is applied to a preamplifying stage basically provided by the transistor 3 with a very high inductance or impedance 4 for the minimum ohmic resistance and maximum tension of the transistor collector. Transistor 4 provides reinforcement to (boosts the output of) the signals to be applied to the driver or exciter transistor 5. The driver transistor 5 amplifies the boosted oscillating stage output and delivers the resulting signals to the resonant circuit 6. Resonant circuit 6 is made up of a radio frequency for coupling to the transistor 7 with the individual resistance 8. Another transistor forms the power amplifier at an output stage 9 with its individual resistance 10. Transistor 9 is provided just in case a higher power is required. This output stage is completed by the high frequency transformer 11 including a secondary winding with its terminals 1 and 12 respectively connected to the active tool U and to the neutral electrode N. The transformer 11 is arranged with a center housing wherein an aluminum cylinder 13 is inserted. Aluminum cylinder 13 basically performs two functions: to dissipate any heat generated by said transformer and to reduce inductance and thereby increase the resonance frequency.

This general circuit is also to be provided with a feeding stage or power stage.

The tool U comprises a plate shaped active electrode A which will smoothly contact and/or slide on the area to be treated of the patient by slightly massaging the patient's body. Electrode A is outwardly electrically insulated by a layer B of a suitable plastic material and is arranged by fitting it in a handle which is very easily operated and handy. This electrode is a holder of the high frequency energy, which does not establish any direct contact with the patient's epidermis, thus removing any possibility of producing sparks or arcing. The metal part of the electrode A forms as a capacitor with the epidermis.

Advantageously, prior to the application of the active electrode A on the epidermis, a suitable cream may be spread thereon. Thus, the electrode allows the device to perform capacitively and concentrate low power energy at the interior of the person's pertinent body area by going through the epidermis.

Figure 2:
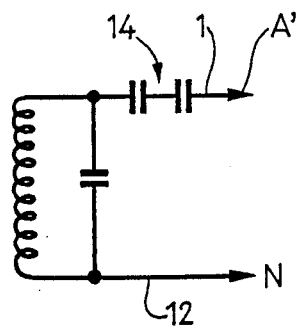
FIG. 2 shows an alternative arrangement of the output transformer.

In FIG. 2, the terminal 1 of the secondary of the transformer 11 of the output stage is connected to the electrode A through two capacitors 14, this latter operation being required in some cases as for example in the depilation tweezers.

Figure 3:
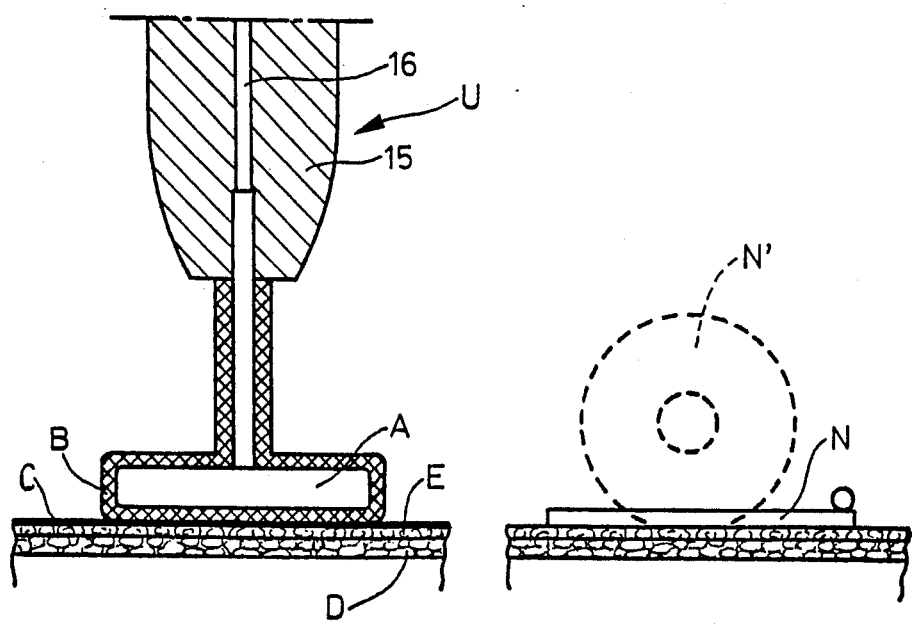
FIG. 3 shows diagrammatically, in an enlarged elevation view, the application of the electrodes and the epidermis.
Figure 4:
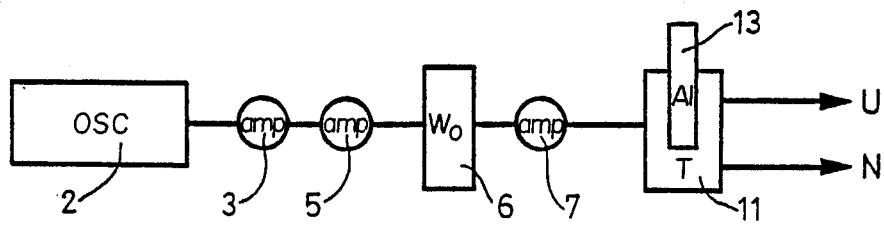
FIG. 4 shows a block diagram of the main portion of the electronic circuit.

As illustrated in FIG. 3, a person's epidermis is shown with reference E and the dermis D. On the epidermis the active metal electrode A is applied to be smoothly slid onto the area to be treated by making a slight massage. This electrode is fitted with a handle 15 making up a tool very easily operated and handy.

Electrode A is connected to the general circuit by a lead 16 and acts as a holder of the high frequency energy which does not establish any direct contact with the epidermis E thus removing any possibility of spark production and resultant burning.

Prior to the application of the active electrode A on the epidermis, a suitable moisturizing cream C is preferably spread on the epidermis. A slight increase in the local temperature with the electronic massage is obtained and controlled by a power control in the arrangement itself, thereby the double function of increasing blood circulation at the area treated and facilitating penetration of cream C through the epidermis expanded pores is obtained.

The neutral electrode N may be a plate-shaped or a cylindrical neutral electrode N' which may be manually grasped by the patient to be treated.

The A handle 15 is provided with suitable components (for instance, a photoelectric cell) to run in the arrangement by digital contact thereon. This arrangement thereby is provided with a suitable automatically connected circuit, which on being activated, is feeding (or powering) the oscillating circuit through a relay and starting an optional operation of the arrangement of the user.

The general circuit is also provided with a feeding or power stage and the arrangement equipped with those proper components for its function as for instance a set of active electrodes of different formal and structural features, for its selective use in accordance with the requirements of each case even by adopting a shape of tweezers or scissors, in this latter case a higher impedance shall be provided to the output coil. These electrodes shall detachably be fitted to the handle to allow the electrode to be interchanged.

It is interesting that during operation of the arrangement there is provided a minimum of cream on the epidermis, even it is better, the cream remains thereon also a few minutes after the electronic massage session. It is understood the length and frequency of the session shall depend in each case on the treating to be performed and the patient receiving it.

While a specific embodiment of the invention has been shown and described in detail to illustrate the application of the principles of the invention, it will be understood that the invention may be embodied otherwise without departing from such principles.

We claim:

1. An electronic device for use in cosmetic and medical treatment of a person by application to the person's epidermis having a load impedance, comprising: high frequency oscillating circuit means for supplying high frequency current in the range of from 1 to 2 megacycles per second and automatically reducing the supplied power when the load impedance is lowered, said high frequency oscillating circuit means including an oscillating circuit producing an oscillating signal at an output, a pre-amplifier having an input and an output, the input being connected to the oscillating circuit output receiving and boosting said oscillating signal, an amplifier having an input connected to the output of the pre-amplifier receiving the boosted oscillating signal and having an output outputting an amplified oscillating signal, resonant circuit means having an input connected to the amplifier output receiving said amplified oscillating signal and having an output outputting an oscillating signal with resonance at an operating frequency, an output amplifier having an input connected to the output of said resonant circuit means receiving the signal output by said resonant circuit means and having an output outputting an amplified signal at an operating frequency, high frequency transformer means having an input connected to the output of the output amplifier and including a first transformer winding connected to the transformer means input, a second transformer winding inductively coupled to the first transformer winding and a center housing located adjacent said second transformer winding, the housing having an aluminum cylinder arranged as a heat sink for dissipating heat generated by said first and second windings and reducing the load inductance of said first and second windings so as to increase the resonance frequency; and, electrical current application means electrically operatively connected to said second winding of said transformer means for transmitting high frequency current capacitively to the epidermis of the person being treated, said electrical current application means including an active electrode and a neutral return electrode, said neutral electrode adapted to be applied on the epidermis to avoid dispersion of electrical current flow.

2. Electronic device according to claim 1, wherein said electrical current application means includes a metal electrode portion connected to said transformer means second winding and an insulated portion surrounding said metal electrode portion said metal electrode portion and said insulated portion forming said active electrode, said insulated portion being adapted to be positioned in contact with the epidermis of the person to be treated thereby allowing the person to be massaged by the active electrode through a moisturizing cream applied to the epidermis.

* * * * *

UNITED STATES PATENT AND TRADEMARK OFFICE
CERTIFICATE OF CORRECTION

PATENT NO. : 4,944,302

DATED : July 31, 1990

INVENTOR(S) : Hernandez, et al

It is certified that error appears in the above-identified patent and that said Letters Patent is hereby corrected as shown below:

On the title page change the related U.S. Application Data from:

Continuation of Ser. No. 880,717, Jul. 11, 1986, abandoned.

to:

Continuation of Ser. No. 880,717, Jul. 1, 1986, abandoned.

Signed and Sealed this

Twenty-second Day of September, 1992

Attest:

DOUGLAS B. COMER

*Attesting Officer*　　　*Acting Commissioner of Patents and Trademarks*